(12) United States Patent
Suzuki et al.

(10) Patent No.: US 7,033,623 B2
(45) Date of Patent: Apr. 25, 2006

(54) MINERAL ABSORPTION ENHANCER

(75) Inventors: Atsushi Suzuki, Haga-gun (JP); Ryuji Ochiai, Haga-gun (JP); Ichiro Tokimitsu, Haga-gun (JP)

(73) Assignee: Kao Corporation, Tokyo (JP)

( * ) Notice: Subject to any disclaimer, the term of this patent is extended or adjusted under 35 U.S.C. 154(b) by 162 days.

(21) Appl. No.: 10/718,716

(22) Filed: Nov. 24, 2003

(65) Prior Publication Data

US 2004/0105908 A1    Jun. 3, 2004

(30) Foreign Application Priority Data

Nov. 26, 2002 (JP) .............................. 2002-342134

(51) Int. Cl.
    *A61K 35/78*    (2006.01)
(52) U.S. Cl. ...................... 424/776; 424/725
(58) Field of Classification Search ............... 424/725, 424/776
    See application file for complete search history.

(56) References Cited

U.S. PATENT DOCUMENTS

| | | | | |
|---|---|---|---|---|
| 3,663,581 A | * | 5/1972 | Lehmann et al. | 554/2 |
| 4,798,732 A | * | 1/1989 | Osawa | 426/542 |
| 5,888,549 A | * | 3/1999 | Buchholz et al. | 426/594 |
| 5,972,409 A | * | 10/1999 | Liu et al. | 426/595 |
| 2002/0051810 A1 | * | 5/2002 | Suzuki et al. | 424/439 |
| 2002/0160067 A1 | * | 10/2002 | Zapp et al. | 424/776 |
| 2003/0003212 A1 | * | 1/2003 | Chien et al. | 426/548 |
| 2004/0091589 A1 | * | 5/2004 | Roy et al. | 426/265 |

FOREIGN PATENT DOCUMENTS

| | | | |
|---|---|---|---|
| FR | 2 648 679 | | 12/1990 |
| JP | 05236918 | * | 9/1993 |
| JP | 06038723 | * | 2/1994 |
| JP | 10-183164 | | 7/1998 |
| JP | 10183164 | * | 7/1998 |
| JP | 2002285026 | * | 10/2002 |
| WO | WO 02/26053 | | 4/2002 |

OTHER PUBLICATIONS

M. Brune, et al., European Journal of Clinical Nutrition, vol. 43, pp. 547-557, "Iron Absorption and Phenolic Compounds; Importance of Different Phenolic Structures", May 15, 1989.

C. Coudray, et al., British Journal of Nutrition, vol. 80, pp. 575-584, "Short-Term Ingestion of Chlorogenic or Caffeic Acids Decreases Zinc but not Copper Absorption in Rats, Utilization of Stable Isotopes and Inductively-Coupled Plasma Mass Spectrometry Technique", 1998.

Yakkyoku, vol. 39, No. 1, pp. 113-117, 1988 (with partial English translation).

* cited by examiner

*Primary Examiner*—Christopher R. Tate
(74) *Attorney, Agent, or Firm*—Oblon, Spivak, McClelland, Maier & Neustadt, P.C.

(57) ABSTRACT

Provided is a mineral absorption enhancing method comprising administering an effective amount of a green coffee bean extract.

The present invention can relieve mineral deficiency by using a mineral absorption enhancer which is excellent in safety and has an excellent mineral absorption enhancing effect.

18 Claims, No Drawings

MINERAL ABSORPTION ENHANCER

TECHNICAL FIELD

The present invention relates to a mineral absorption enhancer which is excellent in safety and mineral absorption enhancing effects and is capable of alleviating mineral deficiency.

BACKGROUND ART

Trace elements important in the medical, nutritional or food science field are 16 elements including sodium, potassium, chlorine, calcium, magnesium, phosphorus and sulfur which are regarded as major minerals, and iron, zinc, copper, manganese, cobalt, chromium, iodine, molybdenum and selenium. These minerals are called essential metals or essential minerals. In spite that their intake amount is trace, they are indispensable elements and must be provided from outside of the body. The National Nutrition Survey 1998 in Japan ("Present Status of National Nutrition in 1998", Ministry of Health, Labor and Welfare), however, expressed misgivings about insufficient iron intake of young women, in addition to insufficiency of calcium intake which has been said for these days.

Minerals have an important function in the living body and when they are deficient, a deficiency disease inherent to deficiency of each of them occurs. For example, iron is effective for qualitative improvement of blood, formation of erythrocytes, stress control, prevention of infectious diseases, increase in the strength of mucous membrane, reinforcement of connective tissue, improvement of immunity, enhancement of resistance to diseases, growth promotion, metabolism promotion of Vitamin B group, improvement of oxygen circulation, activation of brain cells and production of energy. Examples of the symptoms which may occur when iron is insufficient include swelling, incomplete development, wake in a bad temper, cartilage deformity, eczema, hypodynamia, drying of mucous membrane, dizziness, stiffness in the shoulder, reduced vigilance, weakened immunity, shortness of breath, paleness of the skin, getting tired easily, excessive sensitivity to cold, dizziness on standing up, palpitation, low sexual desire, blood from the gums, weakening of connective tissue, hair loss, loss of appetite, nervousness, gait disturbance, angular cheilitis, stomatitis, cheilitis, headache, anemia and noise in the ears.

Zinc is effective for digestion of carbohydrates, synthesis of proteins, assistance in the metabolism of Vitamin $B_1$ or proteins, growth and maturation of sex organs, synthesis of insulin, improvement of the brain function, promotion of wound healing, regulation of Vitamin A metabolism and formation of bones. Examples of the symptoms which may occur when zinc is insufficient include underdevelopment, excessive sensitivity to cold, low wound-healing power, impaired leaning ability, weakening of sexual function, gustatory or olfactory sense disorder, enlarged prostate, arteriosclerosis, accumulation of cholesterol, lowering in resistivity against infections, hair loss, gout, leukemia, cancer, induction of cardiac diseases, diabetes, and pigmented spots.

Calcium serves to form bones and teeth, maintain the cardiac function, cause muscle contraction, relax hypersensitivity, stress or menstrual pain, promote blood clotting, adjust water content in the body, and improve ovulation function. Examples of the symptoms which may appear when calcium is insufficient include osteomalacia, osteoporosis, underdeveloped teeth growth., rickets, palpitation, insomnia, neurosis, arthritis, hypertension, arteriosclerosis, insufficient blood clotting, asthma and nasal allergy.

Magnesium serves to regulate intracellular osmotic pressure, adjust the acid-alkali balance, enhance absorption of Vitamin A group, B group, C, D and E and calcium, prevent deposition of cholesterol, relax mental stress, provide a fine skin, treat nephrolith, prevent diabetes, and prevent alcoholic poisoning. Examples of the symptoms which may occur when magnesium is insufficient include underdevelopment, excessive hypersensitivity, muscle stiffness, convulsion, angina pectoris, myocardial infarction, renal failure, bad complexion, arteriosclerosis, thrombosis, seizure, leukemia and cancer.

At present, deficient minerals are made up for by the administration of tablets, granules or liquids containing the minerals between or after meals. It is however reported that absorption of some of these minerals, for example, iron absorption, is disturbed by catechin contained in a green tea or herb, chlorogenic acid in coffee, or polyphenol in cocoa or wine (Brune M, Rossander L, Hallberg L, "Iron absorption and phenolic compounds: Importance of different phenolic structures", European Journal of Clinic and Nutrition, Vol. 43, 547–558(1989)). It is also reported that coffee disturbs not only the absorption of iron but also that of zinc (Coudray C, Bousset C, Tressol J. Pepin D, Rayssiguire Y, "Short-term ingestion of chlorogenic or caffeic acids decreases zinc but not copper absorption in rats, utilization of stable isotopes and inductively-coupled plasma mass spectrometry technique.", British Journal of Nutrition, vol. 80, 575–584 (1998)). Patients supplemented with iron preparations have been instructed for years not to take beverages such as tea or coffee. (Maro Ishibashi, Toshiro Motoya, "Zusetsu Kusuri no Tainai Dotai (13)", Yakkyoku, Vol. 39, 113–117 (1988).

With popularization of PET-bottled beverages or canned beverages in recent years, tea and coffee have been preferred widely by all age groups. In consideration that there is a fear of young women suffering from iron deficiency as described above, mineral deficiency is a problem to be overcome as soon as possible.

DISCLOSURE OF THE INVENTION

With the foregoing in view, the present inventors have widely searched for natural materials capable of promoting absorption of minerals. As a result, it has been found surprisingly that absorption of minerals existing in food is improved drastically by the intake of an extract of green coffee beans.

In the present invention, there is thus provided the use of a green coffee bean extract for the preparation of a mineral absorption enhancer.

In the present invention, there is also provided a method of enhancing mineral absorption, which comprises administering an effective amount of a green coffee bean extract.

It has been found that intake of the mineral absorption enhancer of the present invention causes a significant increase in a digestibility or percent retention in the body of minerals contained in food. The present invention therefore can provide a food or pharmaceutical composition exhibiting excellent effects for enhancing mineral absorption and preventing or alleviating bad physical conditions or diseases due to mineral deficiency.

BEST MODE FOR CARRYING OUT THE INVENTION

The green coffee bean extract to be used in the present invention is preferably obtained by extracting seeds of *Coffea arabica* LINNE with hot water. The green coffee bean extract in the present invention is available by the process disclosed, for example, in Japanese Patent Application Laid-Open No. Hei 6-38723 or Japanese Patent Application Laid-Open No. Hei 10-183164. For example, it can be obtained by adding hydrous ethanol or water to pulverized green coffee beans, heating the mixture at about 60° C. to 100° C. for about 1 to 10 hours, and after cooling, carrying out separation of an insoluble solid content, hydrolysis and treatment with a porous polymer resin. Alternatively, it can be obtained by collecting the solvent from the extract without hydrolysis of the extract, concentrating the solvent and then subjecting the concentrate to an adsorption treatment with a polymer resin. The green coffee bean extract thus obtained contains about 25 wt. % to about 70 wt. % of a mixture of chlorogenic acid, caffeic acid and ferulic acid, or a mixture of chlorogenic acid and chlorogenic acid homologues calculated on the basis of chlorogenic acids. The chlorogenic acids, that is, chlorogenic acid homologues contained in the green coffee bean extract to be used in the present invention embrace isomers such as chlorogenic acid (5-caffeoyl quinic acid), neochlorogenic acid (3-caffeoyl quinic acid), cryptochlorogenic acid (4-caffeoyl quinic acid), isochlorogenic acid (dicaffeoyl quinic acid), furuloyl quinic acid and feruloyl caffeoyl quinic acid.

The green coffee bean extract has, as indicated in Test later, an effect of promoting digestion and absorption of minerals and is therefore useful as a mineral absorption enhancer. In addition, it is highly safe so that it is useful as a drug, food or drink, specified health food, or quasi-drug for preventing or treating mineral deficiency. In consideration of the conventional knowledge that an extract of roasted coffee beans has an inhibitory action against absorption of iron and zinc, the present invention is utterly beyond expectation.

As the mineral absorption enhancer according to the present invention, a green coffee bean extract containing chlorogenic acid, caffeic acid and ferulic acid may be used as it is or in the dry solid form, or in the form of a composition containing the green coffee bean extract and a proper diluent or carrier. Examples of the diluent or carrier include solid diluents or carriers such as glucose, sucrose, dextrin, cyclodextrin, and gum arabic; and liquid diluents or carriers such as water, ethanol, propylene glycol, glycerin and surfactants. The composition can be provided in a desired form such as liquid, emulsion, paste, powder or granule by using such a diluent or carrier.

When the mineral absorption enhancer of the present invention is used as a food, no particular limitation is imposed on the form of the food. It can be used in any of the forms such as beverages, for example, juice and coffee; liquid foods such as soap; milky or paste foods such as milk and curry; semi-solid foods such as jelly and gummy; solid or powdery foods such as gum, tofu and supplements; and oil or fat-containing foods such as margarine, mayonnaise and dressing, each containing the effective ingredient and ordinarily employed food additives.

When the mineral absorption enhancer of the present invention is used as a drug, the effective ingredient itself or a mixture thereof with a pharmaceutically acceptable carrier can be used as an orally administrable composition. Examples of the orally administrable composition include tablets, granules, fine subtilaes, pills, powders, capsules (including hard capsules and soft capsules), troches, chewables and liquids (drinkable preparations).

The mineral absorption enhancer of the present invention is used as a composition containing a green coffee bean extract as an effective ingredient preferably in an amount of from 0.01 wt. % to 100 wt. %, more preferably, from 0.1 wt. % to 50 wt. %. Although there is no particular limitation imposed on the effective administration amount of the green coffee bean extract in the present invention per adult (weight: 60 kg), the effective administration amount permitting daily intake of from 0.01 to 100 g, particularly preferably from 0.05 to 10 g is preferred.

EXAMPLES

In the below-described Examples, "%" means "wt. %".

Example 1

Composition of a Soft Capsule Film

| | |
|---|---|
| Gelatin | 70.0% |
| Glycerin | 22.9% |
| Methyl paraoxybenzoate | 0.15% |
| Propyl paraoxybenzoate | 0.51% |
| Water | q.s. |
| Total | 100% |

A soft capsule made of the film (oval type, weight: 150 mg) having the above-described composition was filled with 400 mg of a soybean oil and 100 mg of a green coffee bean extract in a conventional manner to yield a soft capsule preparation.

Example 2

The following is an example of a beverage.

| | |
|---|---|
| Skim milk powder | 3.5% |
| Milk casein enzyme hydrolysate | 3.5% |
| Fructose | 9.0% |
| Green coffee bean extract | 0.2% |
| Citric acid | 0.1% |
| Ascorbic acid | 0.1% |
| Flavor | 0.1% |
| Water | 83.5% |
| Total | 100% |

It has been revealed that the beverage having the above-descried composition had a high storage stability and its taste did not present any problem.

Example 3

The following is an example applied to a flour product.

| | |
|---|---|
| Rapeseed oil | 15 g |
| Corn starch | 19 g |
| Wheat flour | 50 g |
| Butter | 5 g |
| Fructose | 14 g |

-continued

| | |
|---|---|
| Green coffee bean extract | 2 g |
| Salt | 0.5 g |
| Baking soda | 0.5 g |
| Water | 10 g |

Cookies having the above-described composition were baked in a conventional manner.

Test

<Method> SD male rats (8 week old) were used for this test. A commercially available solid feed ("MF Feed" manufactured by Oriental Yeast Co., Ltd.) was used as a control diet, while the above-described feed added with 0.5%, 1% or 2% of the green coffee bean extract was used as a test diet. After the rats were fed therewith ad libitum for 2 weeks, they were transferred to a metabolism cage. For 4 days, urine and feces were collected from them and intake and output of iron, zinc, calcium and magnesium were tested. In addition, the blood was collected on the last day of the test to measure iron, zinc, calcium and magnesium levels in the serum. For the detection of minerals, inductively-coupled plasma emission spectrometry (feces), atomic absorption spectrometry (urine), calorimetric assay and atomic absorption spectrometry (serum) were employed. Digestibility (digestion and absorption coefficient) and percent retention in the body of the minerals were calculated in accordance with the below-described equations.

Absorbed amount=intake−output in feces

Digestibility (%)=absorbed amount÷intake×100

Retention in the body=absorbed amount−output in urine

Percent retention in the body (%)=retention in the body÷intake×100

<Statistic Analysis> The results are presented as "mean±standard deviation" (n=5). After confirmation by variance analysis that a significant F value (p<0.05) could be obtained, post hoc test was conducted in accordance with Fisher's PLSD.

<Results> It has been recognized that digestibility (Table 1) and percent retention in the body (Table 2) of the minerals during the intake and output test term showed an increasing tendency dependent on the intake of the green coffee bean extract; and that calcium, iron and zinc levels in the serum were higher when the meal containing the green coffee bean extract was fed than when the control meal (Table 3) was fed.

TABLE 1

Digestibility of minerals

| | Fe digestibility (%) | Zn digestibility (%) | Ca digestibility (%) | Mg digestibility (%) |
|---|---|---|---|---|
| Control diet | 25.1 ± 2.8 | 6.9 ± 7.3 | 21.4 ± 5.1 | 12.4 ± 8.2 |
| Diet containing 0.5% green coffee bean extract | 34.3 ± 0.8 | 11.4 ± 7.3 | 26.8 ± 8.5 | 17.5 ± 7.5 |
| Diet containing 1.0% green coffee bean extract | 35.0 ± 1.9** | 26.1 ± 11.2** | 31.4 ± 5.0* | 22.1 ± 7.7 |
| Diet containing 2.0% green coffee bean extract | 33.6 ± 2.7** | 23.6 ± 8.5** | 29.1 ± 5.6 | 20.5 ± 7.7 |

Mean ± SD (n = 5), *p < 0.05, **p < 0.01 vs. control diet

TABLE 2

Retention of minerals in the body

| | Fe retention in the body (%) | Zn retention in the body (%) | Ca retention in the body (%) | Mg retention in the body (%) |
|---|---|---|---|---|
| Control diet | 22.2 ± 5.1 | 5.1 ± 1.5 | 20.9 ± 5.1 | 9.1 ± 6.9 |
| Diet containing 0.5% green coffee bean extract | 32.2 ± 5.5** | 6.8 ± 7.6 | 26.6 ± 8.5 | 16.9 ± 7.6 |
| Diet containing 1.0% green coffee bean extract | 31.7 ± 4.0** | 19.5 ± 11.0** | 30.8 ± 5.0* | 20.1 ± 7.0* |
| Diet containing 2.0% green coffee bean extract | 30.8 ± 6.3** | 17.4 ± 9.3** | 28.7 ± 5.6 | 18.5 ± 8.2 |

Mean ± SD (n = 5), *p < 0.05, **p < 0.01 vs. control diet

TABLE 3

Serum mineral level

| | Fe level (µg/dl) | Zn level (µg/dl) | Ca level (µg/dl) | Mg level (µg/dl) |
|---|---|---|---|---|
| Control diet | 189.0 ± 66.7 | 108.4 ± 7.9 | 10.70 ± 0.14 | 1.98 ± 0.13 |
| Diet containing 0.5% green coffee bean extract | 295.2 ± 99.3* | 108.8 ± 14.5 | 10.54 ± 0.21 | 1.82 ± 0.35 |

TABLE 3-continued

Serum mineral level

| | Fe level (µg/dl) | Zn level (µg/dl) | Ca level (µg/dl) | Mg level (µg/dl) |
|---|---|---|---|---|
| Diet containing 1.0% green coffee bean extract | 228.4 ± 54.2 | 119.8 ± 13.3 | 10.56 ± 0.32 | 2.02 ± 0.08 |
| Diet containing 2.0% green coffee bean extract | 255.4 ± 53.4 | 125.0 ± 6.8* | 11.10 ± 0.25* | 2.08 ± 0.19 |

Mean ± SD (n = 5), *p < 0.05, **p < 0.01 vs. control diet

The invention claimed is:

1. A method of treating mineral deficiency in a subject in need thereof, comprising:
   administering to said subject an effective amount of a green coffee bean extract.

2. The method according to claim 1, wherein the mineral is at least one selected from the group consisting of iron, zinc, calcium magnesium and mixtures thereof.

3. The method according to claim 1, wherein absorption of a mineral existing in food is increased in said subject.

4. The method according to claim 1, wherein absorption of a mineral existing in a pharmaceutical composition is increased in said subject.

5. The method according to claim 1, wherein a disease due to mineral deficiency is treated.

6. The method according to claim 1, wherein said green coffee bean extract is obtained by extracting seeds of *Coffea arabica* LLNNE with hot water.

7. The method according to claim 1, wherein the green coffee bean extract contains about 25 wt. % to about 70 wt. % of a mixture of chlorogenic acid, caffeic acid and ferulic acid, or of a mixture of chlorogenic acid and chlorogenic acid homologues calculated on the basis of chlorogenic acids.

8. The method according to claim 1, wherein said green coffee bean extract comprises at least one member selected from the group consisting of chlorogenic acid, neochlorogenic acid, cryptochlorogenic acid, isochlorogenic acid, furuloyl quinic acid, feruloyl caffeoyl quinic acid and mixtures thereof.

9. The method according to claim 1, wherein said green coffee bean extract comprises chlorogenic acid, caffeic acid and ferulic acid and is in the form of a dry solid, or in the form of a composition containing the green coffee bean extract and a diluent or a carrier.

10. The method according to claim 9, wherein said diluent or carrier are solid or liquid.

11. The method according to claim 9, wherein said composition is a liquid, an emulsion, a paste, a powder or a granule.

12. The method according to claim 1, wherein said green coffee bean extract is in the form of a beverage; a liquid food, a milky or paste food, a semi-solid foods, a solid or powdery food or an oil or fat-containing food.

13. The method according to claim 1, wherein said green coffee bean extract is used alone or in combination with a pharmaceutically acceptable carrier.

14. The method according to claim 4, wherein said pharmaceutical composition is in the form of tablets, granules, fine subtilaes, pills, powders, capsules, troches, chewables or a liquid.

15. The method according to claim 1, wherein said green coffee bean extract is in the form of a composition containing from 0.01 wt. % to 100 wt. % of green coffee bean extract as an effective amount.

16. The method according to claim 1, wherein said green coffee bean extract is in the form of a composition containing from 0.1 wt. % to 50 wt. % of green coffee bean extract as an effective amount.

17. The method according to claim 1, wherein an effective administration amount is daily intake of from 0.01 to 100 g per 60 kg of body weight.

18. The method according to claim 1, wherein an effective administration amount is daily intake of from 0.05 to 10 g per 60 kg of body weight.

* * * * *